(12) United States Patent  
Gaignet et al.

(10) Patent No.: US 8,551,261 B2  
(45) Date of Patent: Oct. 8, 2013

(54) MODULE FOR PURIFYING A FLUID CONTAINING A CLEANING AGENT, AND METHODS OF FABRICATING AND USING THIS KIND OF MODULE

(75) Inventors: Yves Gaignet, Montigny le Bretonneux (FR); Ichiro Kano, Montigny le Bretonneux (FR)

(73) Assignee: EMD Millipore Corporation, Billerica, MA (US)

( * ) Notice: Subject to any disclaimer, the term of this patent is extended or adjusted under 35 U.S.C. 154(b) by 113 days.

(21) Appl. No.: 13/249,713

(22) Filed: Sep. 30, 2011

(65) Prior Publication Data

US 2012/0017942 A1    Jan. 26, 2012

Related U.S. Application Data

(62) Division of application No. 10/571,738, filed as application No. PCT/IB2004/003724 on Oct. 28, 2004, now abandoned.

(30) Foreign Application Priority Data

Oct. 29, 2003  (FR) ...................... 03 12675

(51) Int. Cl.  
*B08B 9/00*  (2006.01)

(52) U.S. Cl.  
USPC .......................... 134/22.1; 210/106

(58) Field of Classification Search  
None  
See application file for complete search history.

(56) References Cited

U.S. PATENT DOCUMENTS

| 4,780,197 A | 10/1988 | Schuman |
| 4,944,875 A | 7/1990 | Gaignet |
| 5,993,753 A | 11/1999 | Davidson |
| 6,074,551 A | 6/2000 | Jones et al. |
| 6,136,201 A | 10/2000 | Shah et al. |
| 6,325,926 B1 | 12/2001 | Hansen |
| 6,485,641 B1 | 11/2002 | McLeod |
| 2007/0187309 A1 | 8/2007 | Gaignet |

FOREIGN PATENT DOCUMENTS

| EP | 0818228 A1 | 1/1998 |
| JP | 63-141695 U | 9/1988 |
| JP | 5-37329 U | 5/1993 |
| JP | 6-15744 A | 1/1994 |
| JP | 6-48885 U | 7/1994 |
| JP | 6-233981 A | 8/1994 |
| JP | 10-201842 A | 8/1998 |
| JP | 11-28318 A | 2/1999 |
| WO | 03/080128 A1 | 10/2003 |

OTHER PUBLICATIONS

International Search Report and Written Opinion received for PCT Patent Application No. PCT/IB2004/003724, mailed on Jan. 13, 2005, 7 pages.  
International Preliminary Report on Patentability received for PCT Patent Application No. PCT/IB2004/003724, issued on May 1, 2006, 5 pages.  
Office Action Received for Japanese Patent Application No. 2006-537485, mailed on Mar. 31, 2009, 3 pages of English Translation Only.

*Primary Examiner* — Eric Golightly  
(74) *Attorney, Agent, or Firm* — EMD Millipore Corporation

(57) ABSTRACT

Described herein is a disposable module for purifying a fluid, in particular water, adapted to form part of a fluid purification system and method of cleaning at least a portion of a fluid purification system using such a disposable module, where the method includes the steps of: (a) providing a disposable module which includes a housing containing a cleaning agent from the outset: (b) connecting the module to a purification system which is downstream of the module and starting a system cleaning procedure, thereby to clean at least a portion of the purification system.

8 Claims, 2 Drawing Sheets

Figure 1:
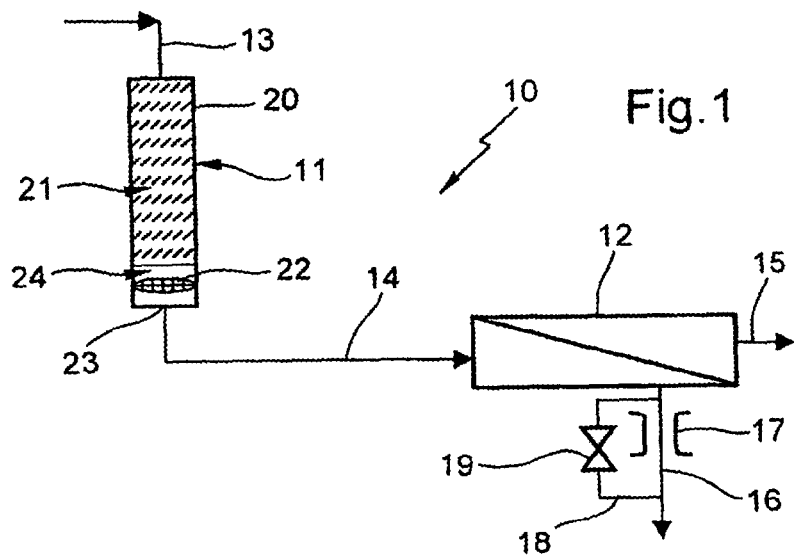

MODULE FOR PURIFYING A FLUID CONTAINING A CLEANING AGENT, AND METHODS OF FABRICATING AND USING THIS KIND OF MODULE

This application is a divisional of U.S. patent application Ser. No. 10/571,738, filed Mar. 14, 2006, which is a 371 of PCT/IB2004/003724, filed on Oct. 28, 2004, which claims priority of French Patent Application No. 0312675, filed on Oct. 29, 2003, the disclosures of which are incorporated herein by reference.

The present invention relates to cleaning a system for purifying a fluid, in particular water, to which at least one module for purifying the fluid is connected for this purpose.

It is aimed more particularly at systems combining means for effecting a purification pretreatment of the fluid, such as activated charcoal, polyphosphates or front filtration members, and means for effecting a purification treatment of the fluid by tangential filtration, such as reverse osmosis or ultrafiltration cartridges housed in one or more modules arranged in series in the system.

To guarantee correct operation of the system, it is necessary to clean, and in particular to disinfect, the component parts regularly, in particular the purification means employing tangential filtration.

In one prior art arrangement, using a message displayed on a screen, the system regularly prompts the user to introduce a cleaning agent into the system via an orifice of the system communicating with a pipe through which the fluid passes or an orifice formed in the receptacle of a purification module that may be recycled, i.e. a module in which the purification means housed in the receptacle, such as the reverse osmosis cartridge, for example, are replaced periodically.

On this occasion, the user is obliged to handle the cleaning products, for example tablets containing soda or chlorine, which are generally harmful to humans because of their caustic, irritant, toxic, etc. nature.

Another prior art system described in U.S. Pat. No. 6,074,551 is provided with a device which, during a cleaning cycle, automatically injects an acidic or basic solution into a recycling pipe supplying one or more reverse osmosis modules with water to be purified.

The present invention aims generally to improve the systems referred to above. One particular object of the present invention is an arrangement for ensuring the safety of the user at the lowest cost.

To be more precise, a first aspect of the present invention consists in a disposable module for purifying a fluid, in particular water, adapted to form part of a fluid purification system and comprising fluid purification means, a housing in which the purification means are housed, and means for removably connecting the purification module to the purification system to establish fluid communication between the purification system and the purification module, characterized in that the housing contains from the outset a cleaning agent disposed to come into contact with the fluid caused to circulate inside the housing to clean at least a portion of the purification system.

In other words, the invention exploits the possibility of using disposable modules, and thus of replacing them periodically, to introduce a cleaning agent into the fluid purification system to clean at least part thereof.

As a result, the fluid purification system is cleaned by applying very simple measures, with the benefit of cost reduction.

Furthermore, the cleaning process may be effected safely since the module supplied to the user already contains the cleaning agent.

This results in a module that not only purifies the fluid but also distributes the cleaning agent into at least a portion of the module itself and/or at least a portion of the remainder of the fluid purification system.

According to preferred, and where applicable combined, features of modules conforming to the invention:

the housing may not be demounted;

the cleaning agent is disposed between an inlet for fluid to be treated formed in the housing and the purification means or between the latter and a purified fluid outlet formed in the housing;

the cleaning agent is housed in a space created for this purpose in the housing, in particular a recess in a raised portion of the housing;

said space is delimited by retaining means for the cleaning agent preferably taking the form of a cage, in particular an added cage;

the housing contains tangential filtration purification means, in particular purification means employing reverse osmosis, nanofiltration, ultrafiltration or microfiltration;

the housing contains fluid purification pretreatment means upstream of the purification processing means, where applicable tangential filtration purification processing means, and the cleaning agent is disposed between the pretreatment means and the purification treatment means or between the latter and a purified fluid outlet formed in the housing;

the pretreatment means are selected from the group comprising ion exchanger activated supports or resins, activated charcoal, chlorine reduction agents, in particular alloys such as copper-zinc formulations (in particular of the KDF® type from FLUID TREATMENT INC.), front filtration members, tartar formation reduction agents, in particular polyphosphates, and combinations of the above;

the cleaning agent comprises a chemical compound or an association of chemical compounds for destroying a biofilm and/or having a bactericidal effect and/or for eliminating organic and/or mineral soiling.

The invention has the further advantage of enabling the use of cleaning agents taking forms as diverse as powders, crystals, granules, tablets, where applicable coating or constituting the contents of capsules or sachets that dissolve or split in contact with the fluid, or in the form of a liquid constituting the content of an enclosure that is split in contact with the fluid.

The cleaning agent is preferably a chlorinated product, an organochlorinated product, an oxidizing product, an acid, a base or a disinfectant solution.

In practice, the cleaning agent is preferably bleach, a chloramine, hypochloric acid, hypochlorous acid, citric acid, tartaric acid, acetic acid, perchloric acid, peracetic acid, a salt of any of the above acids, sodium hydroxide, potassium hydroxide, potassium permanganate, potassium dichromate or a disinfectant solution containing hydrogen peroxide and peracetic acid or organic complexes including silver salts.

Furthermore, the arrangement of the invention advantageously lends itself to an improvement whereby the casing comprises means allowing the module to be identified by the fluid purification system, whereby the latter may, for example, start a cleaning cycle automatically, i.e. without the user having to start the cycle manually, for example by pressing a key of control means of the system.

The invention also consists in a system for purifying a fluid including at least one fluid purification module as defined above.

It further consists in a method of fabricating the above kind of module, including mounting purification means in a casing, characterized in that it further includes placing a cleaning agent inside the casing before closing it.

The invention further consists in a method of cleaning at least a portion of a fluid purification system, characterized in that it includes the steps of connecting a disposable fluid purification module as defined above to the fluid purification system and then starting a system cleaning procedure, where applicable starting said cleaning procedure automatically following identification of the module by the system by means of the identification means.

The features and advantages of the invention will emerge further from the following description, which is given by way of example and with reference to the appended diagrammatic drawings, in which:

FIG. 1 is a diagrammatic representation of the configuration of a fluid purification system using a fluid purification module according to the invention, and FIGS. 2 to 5 represent other embodiments of a fluid purification module of the invention.

In the embodiment shown, a water purification system 10 according to the invention for purifying water comprises, in a manner that is known in the art, a pretreatment module 11 and a reverse osmosis module 12 downstream of the pretreatment module 11.

The reverse osmosis module 12 is not in itself relevant to the present invention and is not described in detail here.

Suffice to say that, in the embodiment shown, it is of the same kind as the TW30 module from DOW CHEMICAL®.

In practice, in this kind of reverse osmosis module 12, the flow of water to be purified is continuous and tangential relative to dense membranes of the module, so that the water to be purified is divided at the membranes into two portions with different concentrations:

a portion that passes through the membranes and is known as the permeate, and a portion that does not pass through the membranes, is known as the retentate, and contains ions, molecules or particles retained by the membranes, in particular mineral ions.

Thus the water produced by a system 10 of the above kind may be considered to have a very low level of dissolved salts (i.e. to be ultrapure water).

In the embodiment shown, the water to be purified comes from the drinking water main, for example, and is fed to the pretreatment module 11 via an inlet pipe 13. The water leaving the pretreatment module 11, after undergoing a purification pretreatment therein, is fed to the reverse osmosis module 12 via a supply pipe 14 of the latter. This is also known in the art.

At the outlet from the reverse osmosis module 12, the permeate (i.e. the ultrapure water) is evacuated via an evacuation pipe 15 and the retentate is fed to the outlet of the water purification system 10 via a retentate (i.e. rejected water) evacuation pipe 16.

The evacuation pipe 16 comprises a restriction 17, i.e. a component reducing the water flowrate and creating a pressure drop in the vicinity of the outlet of the evacuation pipe 16. This is also known in the art. If necessary, the restriction 17 may be bypassed by means of a bypass pipe 18 provided with a shunt valve 19.

As is the case in the embodiment shown, in accordance with the invention, the water purification pretreatment module 11 comprises a housing 20 containing purification pretreatment means, which here take the form of grains of activated charcoal 21, and a cleaning agent 22 disposed between the pretreatment means 21 and the outlet 23 of the module, to which the supply pipe 14 of the reverse osmosis module 12 is connected.

To be more precise, the water purification pretreatment module 11 comprises a housing 24 in which the cleaning agent is placed from the outset so that it is in the flow path of water inside the casing 20 and therefore dissolves in contact with the water and thus cleans all of the portion of the water purification system 10 that is downstream of the water purification pretreatment module 11, in particular the reverse osmosis module 12.

To this end, in the embodiment shown, the cleaning agent 22 in practice takes the form of a chlorinated tablet, as is known in the art, whose role is to destroy bacteria and prevent their proliferation downstream of the pretreatment module 11, and in particular in the reverse osmosis module 12, that is to say, more generally, to disinfect this portion of the water purification system 10.

It should also be noted that the casing 20 comprises means, not shown, for identification of the module 11 by the water purification system 10, which enables the latter to start a cleaning cycle automatically after connection of the pretreatment module 11 to the remainder of the water purification system 10 and recognition of the module 11 by the system 10.

Figure 2:
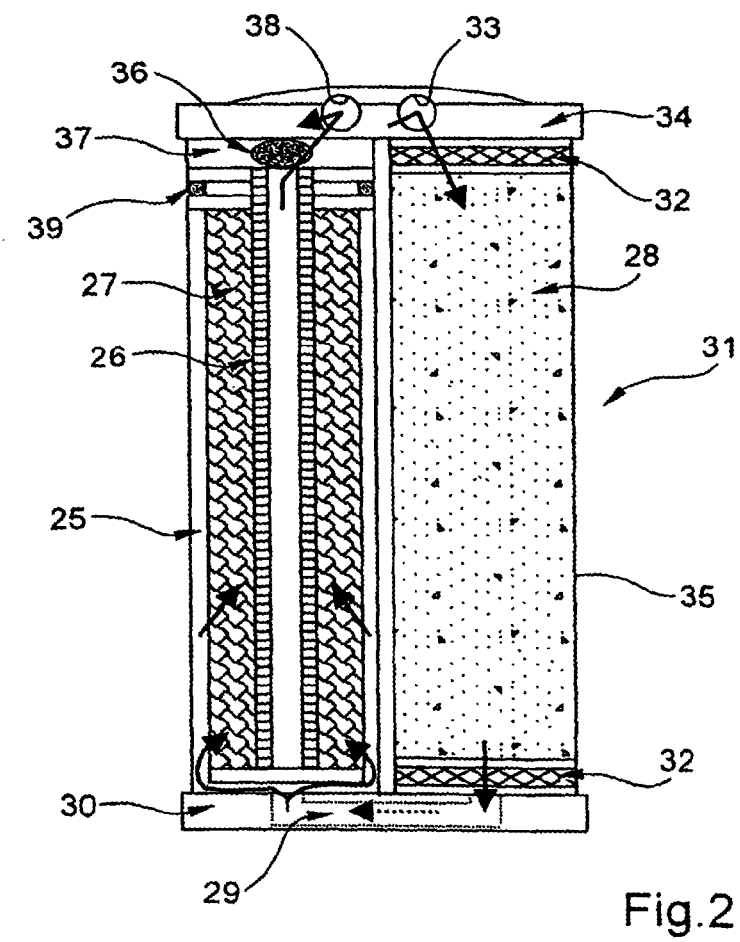

The cleaning agent may be placed elsewhere, for example in other embodiments of the water purification module, and in particular:

1) As shown in FIG. 2, downstream of a filter cartridge 25 of the kind comprising a perforated tube 26 surrounded by an annular layer 27 of filter material and preceded by a mass 28 of filter material, activated charcoal grains in this example, with which there is fluid communication via a passage 29 formed in the bottom 30 of the module 31. The mass of filter material 28 is retained by separator members 32 and is in fluid communication with an inlet 33 for fluid to be purified that is provided in a cover 34 of the cylindrical casing 35 of the purification module 31 shown in FIG. 2. Here the cover 34 is welded or stuck to the casing 35 so that it may not be removed.

The cleaning agent tablet 36, which is also a chlorinated tablet here, is disposed in a housing 37 especially provided for this purpose in the housing 35 between the cartridge 25 and a purified fluid outlet 38 formed in the cover 34 of the housing 35. It is clamped in place between the upper end of the tube 26 of the filter cartridge 25 and the cover 34 of the housing 35.

An O-ring 39 provides a seal between the inlet and the outlet of the filter cartridge 25.

Figure 4:
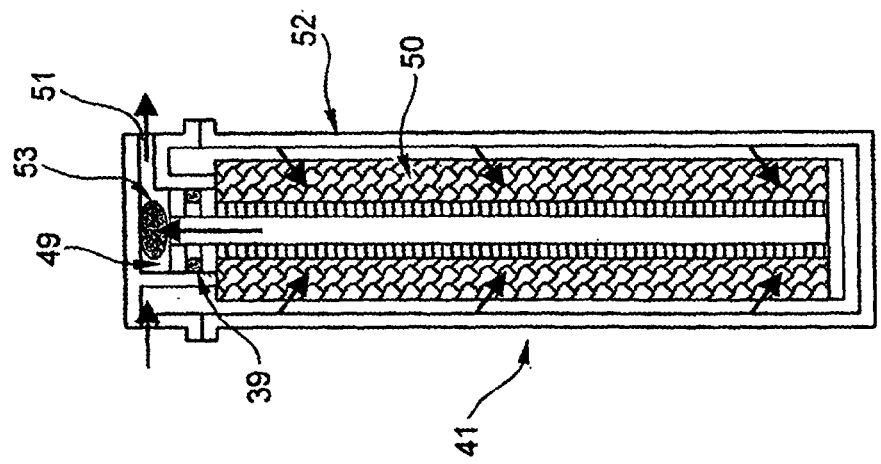
Figure 3:
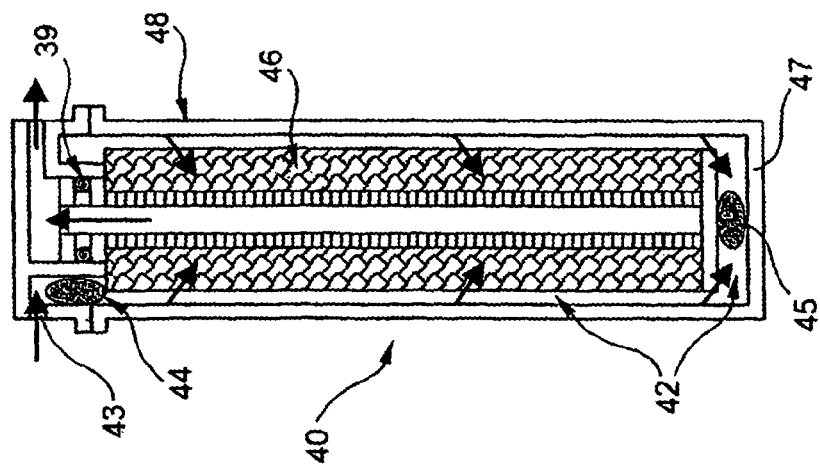

2) In the embodiments shown in FIGS. 3 and 4, the module is similar to that shown in FIG. 2, but the module 40 or 41 contains only one cartridge of the kind shown in FIG. 2, and it may be seen that a cleaning agent tablet, also of the kind shown in FIG. 2, may be placed either (i) in an existing free space 42 in the module 40, either in the immediate vicinity of the inlet 43 for water to be purified (FIG. 3, tablet 44) or further downstream in the water flow passage (FIG. 3 tablet 45, sandwiched between the bottom end of the cartridge 46 and the bottom 47 of the housing 48 of the module 40), or (ii) in a free space 49 between the upper end of the cartridge 50 and an outlet 51 for water to be purified from the housing 52 of the module 41 (FIG. 4 tablet 53).

In connection with FIG. 3, it should be noted that a plurality of tablets may be placed in the same module.

What is more, in the embodiments shown in FIGS. 3 and 4, it is interesting to note that the tablets are held in place by the existing structural members of the housing and, where applicable, by the member that it contains.

Figure 5:
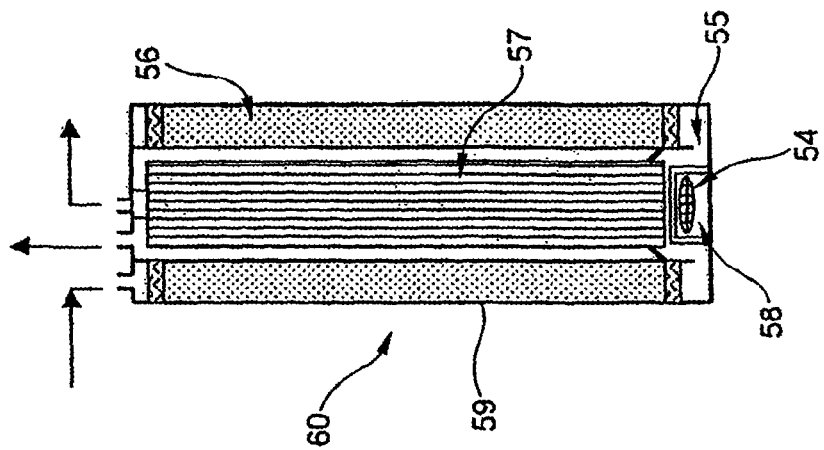

Finally, in the embodiment shown in FIG. 5, a tablet 54 is placed in the passage 55 for the flow of water coming from the pretreatment means 56 (here grains of activated charcoal) and entering a reverse osmosis cartridge 57. It is placed in a space 58 created for this purpose that is simply molded in one piece with the housing 59 of the module 60, which has cost benefits.

In further embodiments, the tablet may be disposed in a recess formed in an upstanding portion of the housing, in a cage added to or separate from the housing, etc.

Note further that the means for connecting the modules removably to the purification system, for them to form an integral part thereof and to establish water communication between the latter and the module and vice-versa, are not shown in the figures. For example, they may be means of the kind described in European patent application EP-A-0 818 228 in the name of Niermeyer et.al.

In all other respects, these modules are of conventional structure: they are therefore not described in more detail here.

As may be seen in FIGS. 1 to 5, none of the housings 20, 35, 48, 52 and 59 described here has an opening for introducing cleaning agent into the interior thereof subsequent to its production.

It must further be noted that in practice all the modules that have just been described may be equipped with means for identification of the module by the fluid purification system, thanks to which the latter may, for example, start a cleaning cycle automatically after connection of the module to the system and identification thereof by the system.

Finally, it should also be noted that chlorinated tablets may be replaced by any other type of cleaning agent of the kind defined hereinabove and that the treatment and pretreatment means used in the embodiment shown in FIGS. 2 to 5 may equally be replaced by other, corresponding means, also of the kind defined above.

Of course, the present invention is not limited to the embodiments described and shown, and encompasses any variant execution thereof.

The invention claimed is:

1. A method of cleaning at least a portion of a fluid purification system comprising the steps of:
   (i) providing a disposable pretreatment module comprising a housing comprising one or more of ion exchanger activated supports, ion exchanger activated resins, activated charcoal, chlorine reduction agents, front filtration members, and tartar formation reduction agents, wherein the housing contains a cleaning agent from the outset and wherein the housing is not demounted;
   (ii) connecting the disposable pretreatment module to the fluid purification system, such that the fluid purification system is downstream of the disposable pretreatment module and is in fluid communication with the module; and
   (iii) starting as system cleaning procedure,
   wherein the cleaning agent is disposed to come into cornet with a fluid caused to circulate inside the housing after step (iii), thereby to clean at least a portion of the fluid purification system.

2. The method of claim 1, wherein the disposable pretreatment module is removably connected to the fluid purification system.

3. The method of claim 1, wherein the cleaning procedure starts automatically, without a user having to start the cleaning procedure.

4. The method of claim 1, wherein the cleaning agent comprises a chemical compound or an association of chemical compounds for destroying a biofilm and/or having a bactericidal effect and/of for eliminating organic and/or mineral soiling.

5. The method of claim 1, wherein the cleaning agent is in a form selected from the group consisting of powder, crystals, granules, tablets, capsules, or sachets.

6. The method of claim 1, wherein the cleaning agent is selected from the group consisting of a chlorinated product, an organochlorinated product, an oxidizing product, an acid, a base or a disinfectant solution.

7. The method of claim 1, wherein the cleaning agent is housed in a recess in a raised portion of the housing.

8. The method of claim 1, wherein the cleaning agent is housed in a space in the housing.

* * * * *

UNITED STATES PATENT AND TRADEMARK OFFICE
CERTIFICATE OF CORRECTION

| | | |
|---|---|---|
| PATENT NO. | : 8,551,261 B2 | Page 1 of 1 |
| APPLICATION NO. | : 13/249713 | |
| DATED | : October 8, 2013 | |
| INVENTOR(S) | : Yves Gaignet et al. | |

It is certified that error appears in the above-identified patent and that said Letters Patent is hereby corrected as shown below:

In the Claims:

In column 6, Line 11, in Claim 1, delete "as" and insert -- a --, therefor.

In column 6, Line 12, in Claim 1, delete "cornet;" and insert -- contact; --, therefor.

Signed and Sealed this
Eleventh Day of February, 2014

Michelle K. Lee
*Deputy Director of the United States Patent and Trademark Office*